(12) United States Patent
Upmeier et al.

(10) Patent No.: US 9,267,953 B2
(45) Date of Patent: Feb. 23, 2016

(54) METHOD FOR DETECTION OF SPECIFIC IMMUNOGLOBULIN CLASS G ANTIBODIES

(75) Inventors: Barbara Upmeier, Iffeldorf (DE); Ralf Bollhagen, Penzberg (DE); Martina Bronold, Wolfratshausen (DE); Frederic Donie, Penzberg (DE); Christine Markert-Hahn, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 270 days.

(21) Appl. No.: 12/817,469

(22) Filed: Jun. 17, 2010

(65) Prior Publication Data

US 2011/0143454 A1 Jun. 16, 2011

Related U.S. Application Data

(63) Continuation of application No. 12/605,568, filed on Oct. 26, 2009, now abandoned, which is a continuation of application No. PCT/EP2008/003623, filed on May 6, 2008.

(30) Foreign Application Priority Data

May 8, 2007 (EP) .................................... 07009240

(51) Int. Cl.
*G01N 33/543* (2006.01)
*G01N 33/68* (2006.01)

(52) U.S. Cl.
CPC ........ *G01N 33/6854* (2013.01); *G01N 33/5438* (2013.01); *G01N 33/54313* (2013.01)

(58) Field of Classification Search
None
See application file for complete search history.

(56) References Cited

U.S. PATENT DOCUMENTS

| | | | | |
|---|---|---|---|---|
| 4,537,861 A | * | 8/1985 | Elings et al. | 436/518 |
| 6,632,655 B1 | * | 10/2003 | Mehta et al. | 506/14 |
| 2003/0003460 A1 | | 1/2003 | Sigal et al. | |

FOREIGN PATENT DOCUMENTS

| EP | 0280211 A2 | 2/1988 |
|---|---|---|
| EP | 1098198 A1 | 5/2001 |
| EP | 0957360 B1 | 7/2002 |
| EP | 0944838 B1 | 9/2003 |
| EP | 1653233 A1 | 5/2006 |
| WO | 98/12539 A1 | 3/1998 |
| WO | 99/15898 A1 | 4/1999 |

OTHER PUBLICATIONS

Martin et al., (Epitope studies indicae that histidyl-tRNA synthetase is a stiumulating antigen in idiopathic myositis, FASEB J. 9, 1995, pp. 1226-1233.*
Nishikai et al., Anti-Jo-1 in Polymyositis or Dermatomyositis: Evaluation by Elisa using Recombinant Fusion Protein JO-1 Antigen, British Journal of Rheumatology 1998; 37; pp. 357-361.*
International Search Report issued Jan. 21, 2009 in PCT Application No. PCT/EP2008/003623.
International Preliminary Report on Patentability issued Nov. 9, 2002 in PCT Application No. PCT/ EP2008/003623.
Benecky, Michael J. et al., Detection of hepatitis B surface antigen in whole blood by coupled particle light scattering (Copalis(TM)), Clinical Chemistry, 1997, pp. 1764-1770, vol. 43, No. 9.
Boas, Gary, Surface plasmon resonance nanosensors help identify biomarkers for Alzheimer's disease, Biophotonics International, Apr. 2005, pp. 60-61, vol. 12.
Bystrak, Semion. et al., A Homogeneous Immunofluorescence Assay Based on Dye-Sensitized Photobleaching, Analytical Biochemistry, 1995, pp. 127-134, vol. 225.
Klaassen, R. J. L. et al., Differentiation between neutrophil-bound antibodies and immune complexes, British Journal of Haematology, 1991, pp. 398-402, vol. 77, No. 3.
Merrill, Gerald A. et al., A quantitative electrochemiluminescence assay for Clostridium perfringens alpha toxin, Analytical Biochemistry, 2006, pp. 181-187, vol. 357, No. 2.
Schaertl, S. et al., A Novel and Robust Homogeneous Fluorescence-Based Assay Using Nanoparticles for Pharmaceutical Screening and Diagnostics, Journal of Biomolecular Screening, Jan. 1, 2000, pp. 227-237, vol. 5, No. 4.
Yin, Xue-Bo et al., 4-(Dimethylamino)butyric Acid Labeling for Electrochemiluminescence Detection of Biological Substances by Increasing Sensitivity with Gold Nanoparticle Amplification, Analytical Chemistry, Jun. 1, 2005, pp. 3525-3530, vol. 77, No. 11.

* cited by examiner

*Primary Examiner* — Gary W Counts
(74) *Attorney, Agent, or Firm* — Dinsmore & Shohl

(57) ABSTRACT

Methods for determining an analyte in a sample by immunoassay in a one-step format without performing washing steps are described. The method includes a first analyte-specific receptor that contains at least two binding sites for the analyte, and a second analyte-specific receptor that selectively binds to an aggregate arrangement of at least two analyte molecules bound to the first receptor.

12 Claims, No Drawings

METHOD FOR DETECTION OF SPECIFIC IMMUNOGLOBULIN CLASS G ANTIBODIES

RELATED APPLICATIONS

This application is a continuation of U.S. application Ser. No. 12/605,568 filed Oct. 26, 2009, now abandoned, which is a continuation of PCT/EP2008/003623 filed May 6, 2008 and claims priority to EP 07009240.8 filed May 8, 2007.

FIELD OF THE INVENTION

The invention concerns a method for the determination of an analyte in a sample by means of an assay which can be carried out in a one-step format without washing steps.

BACKGROUND

The immune system of a mammalian organism produces antibodies which are also known as immunoglobulins as a response to the introduction of foreign substances. They serve as a defense against foreign substances which are also referred to as antigens. The immunoglobulins can be divided into five different classes. One distinguishes between immunoglobulins of the M, G, A, E and D classes. These five immunoglobulin classes differ in the composition of the heavy chain which is referred to as the $\mu$, $\gamma$, $\alpha$, $\epsilon$ and $\delta$ chain, respectively.

Each immunoglobulin class has a different function in the organism. The class M immunoglobulins occur during a first contact with the antigen, the so-called primary immunization. However, the concentration of these immunoglobulins rapidly decreases as the infection progresses. The class G immunoglobulins are firstly slowly formed during a primary immunization and occur in large amounts in a second infection with the same antigen. The class A immunoglobulins are found on the surfaces of the mucous membranes of the organism and are responsible for the local defense processes. The class E immunoglobulins are mainly responsible for allergic reactions. The exact function of the class D immunoglobulins is thus far unknown.

The individual immunoglobulin classes occur in very different concentrations in the blood. Thus, the class G immunoglobulins (IgG) are the most abundant class in normal human serum with a proportion of about 75% which corresponds to a serum content of 8 to 18 mg/ml. The second most frequent immunoglobulin is IgA, the average serum concentration of which is 0.9 to 4.5 mg/ml. Class M immunoglobulins are present at a concentration of 0.6 to 2.8 mg/ml, class D immunoglobulins are present at a concentration of 0.03 to 0.4 mg/ml. The proportion of IgE antibodies is lowest—they only occur in serum at a concentration of 0.02 to 0.05 µg/ml.

Various methods for detecting antibodies of a certain class that are specific for an antigen are described in the prior art. Thus, the detection of antigen-specific antibodies of a certain class in a sample is often carried out by binding specific antibodies to a solid phase coated with the specific antigen. The immunoglobulins (Ig), which are specific for the antigen and are now bound to the solid phase, are detected by the binding of antibodies, which are specifically directed against human Ig of a certain class, to the Ig molecules to be detected. The antibodies directed against human Ig are provided with a label by means of which the detection takes place. However, such a test procedure (indirect test format) is only possible if, before the reaction with the class-specific labelled antibodies directed against human Ig, all unspecific, non-bound Ig is removed by washing. A one-step test procedure such as that, which is often required for automated systems, is thus not possible in this format.

The so-called bridge test opens up a possibility for carrying out an antibody detection in a one-step test. The bridge test concept is described in EP-A-0 280 211. In this method, a first binding partner, which is capable of specific binding to the antibody to be determined such as, for example, an antigen, is bound to a solid phase. The antibody to be determined binds to the solid phase-bound antigen. A further specific antigen, which is provided with a label, is also present in the test mixture. The antibody is detected by means of the label. If immunoglobulins of different classes but of the same specificity are present in the sample, the test does not distinguish between the various classes.

EP 0 944 838 B1 discloses a bridge test detection method that enables the selective determination of antigen-specific IgG antibodies in a sample which also contains IgM antibodies of the same specificity. The antigen is used in a monomeric form for this. The monomeric antigen has the effect that IgM antibodies having the same specificity cannot react or can only weakly react with the antigen.

Specific antibody tests are of major importance in infection serology in which the immune response to antigenic structures of pathogens is detected. Although different sources for obtaining antigens of the pathogens are state of the art (recombinant expression in prokaryotic and eukaryotic systems, controlled culture of the pathogen, isolation of antigens from natural sources) it is not always possible to obtain antigens in monomeric form in order to carry out an IgG-selective immunoassay in a one-step format.

EP 0 957 360 B1 describes the use of rheumatoid factors to reduce the Hook effect in methods for determining an analyte.

EP 1 098 198 A1 describes an immunoassay for the determination of human IgG antibodies. In this case a particular monoclonal antibody is used, which is directed against a conformation epitope of the Fc fragment of human IgG bound to an antigen. This antibody is used for the selective detection of IgG and can differentiate between IgGs that bind to an antigen and IgGs that bind no antigen. However, the presence of unbound IgG interferes and leads to signal losses.

EP 1 653 233 A1 describes a test procedure for the determination of antigen-specific antibodies of the IgG class wherein a sample is brought into contact with a solid phase to which antigens are bound. In this method a monoclonal antibody is used that distinguishes between immunoglobulins unspecifically bound to the solid phase and immunoglobulins bound to the antigen. After contacting the sample with the solid phase, it is washed and, subsequently, the monoclonal antibody is applied.

An immunoassay for detecting antigen-specific immunoglobulin G in a one-step format that can be carried out using automated analyzers is described in the patent application WO 99/15898 (Chien et al.). In Chien et al, an antibody is used which is specific for the constant part of the human immunoglobulin G. In this assay, there is a significant interference by free unspecific IgG without sufficient discrimination between free and complexed IgG.

One-step methods of the prior art for the detection of IgG cannot adequately distinguish between free and bound IgG. In order to discriminate between IgG and IgM of the same specificity, antigens must be monomeric which is a requirement that cannot often be fulfilled.

Hence the object of the present invention was to develop a method for the detection of an analyte in a sample and, in particular, antigen-specific antibodies of the immunoglobulin class G that can be carried out in a one-step method in order to be used advantageously in automated systems. In addition, the present invention has the object of at least partially overcoming the disadvantages of the prior art. For this, it is necessary to adequately discriminate between free analyte and bound analyte.

SUMMARY OF THE INVENTION

In a first aspect, the present invention concerns a method for the determination of an analyte in a sample comprising the steps:
  (a) contacting the sample with a first analyte-specific receptor and a second analyte-specific receptor wherein one of the two receptors is bound to a solid phase or is capable of binding to a solid phase, and the other receptor carries a signal-generating group or is capable of binding to a signal-generating group, and
  (b) detecting the presence and/or the amount of the analyte by determining the signal-generating group on the solid phase, characterized in that the first analyte-specific receptor contains at least two binding sites for the analyte, and the second analyte-specific receptor is capable of selectively binding to an arrangement of at least two analyte molecules which are bound to the first receptor.

It was surprisingly found that the presence of rheumatoid factor in a sample does not interfere with the method according to the invention.

DETAILED DESCRIPTION OF THE INVENTION

The method according to the invention is suitable for detecting any analyte in a sample. It is preferred that the analyte is an antigen-specific antibody, e.g., an antigen-specific antibody of the G, M, A, D and/or E class. The analyte is more preferably an antigen-specific antibody of the G class, e.g., against a pathogen, a tumour antigen and/or an autoantigen.

The sample containing the analyte is preferably a liquid sample. The liquid sample can be any liquid sample, e.g., an aqueous sample. The sample can be a biological sample and/or a clinical sample such as, e.g., a body fluid, such as blood, serum, urine, sputum, pus, etc. A sample can more preferably contain rheumatoid factor.

In a preferred embodiment, the first and the second analyte-specific receptor are different from one another.

In the method according to the invention, the second receptor is capable of selectively binding to an arrangement of at least two analyte molecules which are bound to the first receptor. "An arrangement of at least two analyte molecules" means that the at least two analyte molecules together have a structure to which the second receptor can selectively bind, i.e., which can be recognized by the second receptor, and which the second receptor can distinguish from a single analyte molecule, in particular, from a single analyte molecule that is not bound to the first receptor. "Capable of selective binding to" also means that the second receptor can bind more strongly to the arrangement of at least two analyte molecules than to a single analyte molecule. An arrangement can also be an immune complex comprising at least two analyte molecules, in particular, antibodies, which are bound to the first receptor. The first receptor can comprise an antigen with at least two epitopes.

An "arrangement" preferably contains at least two analyte molecules which are "aggregated" with one another and bound to the first receptor. "Aggregated" or "aggregate" within the sense of the present invention means that the analyte molecules bound to the receptor are at a certain distance from one another, which is selected such that the second analyte-specific receptor binds to the at least two analyte molecules bound to the first receptor. Hence, the analyte molecules bound to the first receptor are in spatial proximity to one another. The distances between the analyte molecules bound to the first receptor are determined by the distance between the binding sites in the receptor. "Aggregated" or "aggregate" in the sense of the present invention comprises that the analyte molecules bound to the first receptor are not chemically bound to one another or have chemical bonds between one another, e.g., covalent bonds or non-covalent bonds such as, e.g., hydrogen bonds or antigen-antibody bonds.

The first analyte-specific receptor contains at least two binding sites for the analyte. The first analyte-specific receptor can contain at least two different binding sites, at least two identical binding sites or a combination of different and identical analyte binding sites.

In yet a further preferred embodiment, the first receptor is an oligomeric or multimeric receptor. "Oligomer" or "multimer," in the sense of the present invention, means that the first receptor contains multiple binding sites for the analyte, preferably at least 3, at least 4, at least 5, at least 10, at least 20, at least 50 or at least 100 binding sites. The first receptor preferably contains up to 200, up to 100, up to 50, up to 20, up to 10 or up to 5 binding sites. "Oligomer" or "multimer," in the sense of the present invention, also includes the meaning that the first receptor can be an oligomer or a multimer of building blocks, where each of the building blocks can have no binding site, one binding site or multiple binding sites. "Oligomer" or "multimer" also encompasses "oligovalent" or "multivalent".

In a further preferred embodiment, the first receptor is provided in the form of receptor precursors. Preferably at least two receptor precursors are provided. The receptor precursors preferably associate with one another or bind to one another in order to form the first receptor. The receptor precursors can be of such a nature that they can associate or bind to one another during step (a) of the method according to the invention in order to form the first receptor. They can also be of such a nature that they can associate or bind to one another before step (a) of the method according to the invention. The at least two receptor precursors can be of such a nature that either one of the receptor precursors comprises all binding sites for the analyte or that both receptor precursors comprise at least one binding site for the analyte.

The at least two receptor precursors can associate with one another or bind to one another by means of a chemical bond where the bond can be covalent or non-covalent. Any binding system that is known to a person skilled in the art can be used for the association or binding. X/anti-X binding systems described herein, such as, e.g., the avidin/streptavidin biotin system, are preferred. Thus, one of the at least two receptor precursors can contain a biotin group and the other receptor precursor contains an avidin or streptavidin group. For example, a biotinylated molecule, e.g., a peptide which carries at least one binding site for the analyte, can form a first receptor by binding to or associating with a bead coated with avidin or streptavidin where the receptor contains at least two binding sites for the analyte. The bead can also be biotinylated and the molecule that carries at least one binding group can be coupled with avidin or streptavidin.

Hence, the first receptor can comprise a bead that carries an arrangement of at least two binding sites for the analyte. It is preferred that the first receptor comprises a bead which comprises at least 10, at least 50, or at least 100 binding sites.

In yet a further preferred embodiment of the method according to the invention, the first receptor comprises an antigen that contains at least two epitopes as binding sites for the analyte. In this embodiment, the analyte is an antibody, preferably an antibody of the G, M, A, D and/or E class, even more preferably, an antibody of the G class.

The antigen according to the invention can be an oligomeric or multimeric antigen. The at least two epitopes can be identical or different. The antigen can comprise at least two different epitopes, at least 2 identical epitopes or a combination of identical and different epitopes. The antigen can comprise a repetitive epitope. The antigen can contain multiple epitopes preferably at least 3, at least 4, at least 5, at least 10, at least 20, or at least 50 epitopes. The antigen can contain up to 100, up to 50, up to 20, up to 10, or up to 5 epitopes.

The antigen according to the invention can have any epitopes with different structural features and compositions. The antigen can comprise a microorganism, a cell, a cell organelle, a cell compartment or a lysate or a preparation thereof, e.g., a membrane preparation. The antigen can be an antigen isolated from a natural source or an antigen produced by recombinant expression in prokaryotic and/or eukaryotic organisms and/or by chemical synthesis. Oligomerization or multimerization of the antigen can optionally be brought about by natural assembly or aggregation, or by targeted adsorptive or covalent linkage, or by adsorptive or covalent coupling.

In a further preferred embodiment, the second analyte-specific receptor comprises an antibody. Antibodies with rheumatoid factor-like properties that can preferably bind aggregated or oligomerized immunoglobulins, but not single immunoglobulins are more preferred.

It is likewise preferred that the second receptor comprises an antibody having a low affinity for the binding of the analyte. The affinity of an antibody, according to the invention, is defined as the strength of all non-covalent interactions between the individual antigen binding site on an antibody and the individual epitope. Antibodies having low affinity bind weakly and dissociate rapidly, whereas high affinity antibodies bind more strongly and can remain bound for a longer period.

The affinity at a binding site does not always reflect the actual strength of an antigen-antibody interaction, such as, e.g., between the antigens according to the invention as first receptors having at least two epitopes to which analyte molecules, e.g., antigen-specific antibodies are bound, and, e.g., antibodies having multiple binding sites as second receptors. The interaction between antigen and an antigen binding site of an antibody at one site increases the probability of a reaction at a second antigen binding site of the same antibody which can result in a cross-linking of the interaction partners. The strength of such multiple interactions between a multivalent antibody and antigen is referred to as avidity. In this connection, a high avidity compensates a low affinity such as, e.g., in the case of the pentameric immunoglobulin IgM.

In a preferred embodiment, the second receptor is an antibody which comprises at least two, at least three, at least four, at least five, and particularly preferably, 10 or more paratopes.

In the present invention, the second receptor more preferably comprises an antibody of low affinity and high avidity for the analyte, e.g., an antigen-specific antibody comprising at least two, at least three, at least four, at least five and especially preferably, 10 or more paratopes. An even more preferred second receptor is an antigen-specific antibody of the immunoglobulin class IgM or IgG immunoglobulins cross-linked to one another. The antibody <h-agg.IgG> IgM is most strongly preferred.

The low-affinity antibodies according to the invention preferably have an affinity coefficient of more than $10^{-8}$ M, preferably, of more than $10^{-7}$ M and more preferably, of more than $10^{-6}$ M.

The low-affinity antibody according to the invention as the second receptor preferably recognizes analyte molecules, in particular, antigen-specific antibodies which are bound, e.g., in a sufficient density, in an arrangement and/or as an aggregate to the first receptor. Unbound analyte molecules or analyte molecules that are unspecifically bound on the first receptor, which are loosely and irregularly distributed are preferably not recognized or only to a negligible extent. Such a second analyte-specific receptor according to the invention is thus capable of selectively binding to a first receptor having at least two analyte molecules bound thereto.

Antibodies of the IgM class have the properties of the general rheumatoid antibody class, i.e., they preferably bind antigen-specifically bound antibodies of the immunoglobulin class IgG because they only recognize the sufficiently densely packed antigen-specific antibodies on the multimeric antigen of the immunoassay. Non-complexed, free immunoglobulins G which, in particular, are not specific for the antigen are not recognized or only to a negligible extent.

In this manner, it is possible for example to detect antigen-specific IgG in the presence of immunoglobulins of other classes having the same antigen specificity and also in the presence of unspecific IgG without loss of sensitivity which would impair the assay. The use of the second receptor according to the invention enables a high discrimination to be achieved between antigen-specifically bound immunoglobulin G and non-antigen-specific, free IgG. Further, the second receptor according to the invention preferably recognizes the immunoglobulin molecules that are specifically bound and located next to one another on the antigen according to the invention and can be oligomerized; but it does not recognize or recognizes to a negligible extent free, uncomplexed, antigen-specific immunoglobulins.

Thus, the detection of antigen-specific immunoglobulins of the class G in a sample in the presence of naturally occurring, non-antigen-specific IgG molecules that are present in excess in a one-step format is ensured.

A "one-step method" is understood to mean that the reaction of the analyte with the reactant according to the invention can be carried out in one reaction mixture and, in particular, without having to separate components of the mixture from one another by one or more washing steps.

"One-step method" or "reaction in one reaction mixture" includes the possibility of adding the reactants simultaneously/successively to the reaction mixture (sample), and/or of adding further auxiliary substances (e.g., buffers, salts, etc.) simultaneously/successively.

A preferred "one-step method" is carried out without a washing step.

In another preferred embodiment step (a) in the method according to the invention is carried out in one reaction mixture without a washing step. More preferably steps (a) and (b) are carried out in one reaction mixture without a washing step. The method according to the invention enables antigen-specific antibodies of the immunoglobulin class G to be detected in a one-step format. These antibody tests are of particular importance in the in-vitro diagnosis of infectious diseases and autoimmune diseases.

In other embodiments, the method according to the invention can comprise a washing step.

In a most preferred embodiment, the first receptor in the method according to the invention is an antigen according to the invention, the second receptor is a rheumatoid factor-like antibody, in particular an immunoglobulin of the M class and the analyte is an antigen-specific immunoglobulin G. Thus, binding of multiple specific immunoglobulins G to the antigen binding partner is possible, which can result in an oligomerization of the IgG molecules, i.e, two or more IgGs can be in spatial proximity to one another and, as a result, become capable of binding to the rheumatoid factor-like receptor.

In yet a further preferred embodiment, the method according to the invention is a diagnostic method, in particular for the detection of antibodies in biological samples, in particular, clinical samples. In the diagnostic method according to the invention, it is, for example, possible to detect antibodies against a pathogen, e.g., a virus or a microorganism, against a tumor antigen and/or autoantibody. In particular it is possible to detect antibodies against viruses such as rubella, CMV, HAV, HBV, and HCV.

In the method according to the invention, antibody fragments can also be used as receptors. The fragmentation of antibodies is known to a person skilled in the art and is carried out according to conventional techniques. Examples of proteolytically cleaved and/or recombinantly produced fragments include Fab, F(ab')2, Fab', Fv and single-strand antibodies (scFv) which contain a V[L] and/or V[H] domain with a peptide linker. The scFvs can be covalently or non-covalently linked to form an antibody with two or more binding sites. The antibody according to the invention can be a polyclonal, monoclonal, chimeric or humanized antibody, which can be recombinantly produced. It is preferred that the second receptor is a monoclonal antibody.

The antibody according to the invention is preferably a monoclonal antibodym in particular, of the IgM class having the property of a low affinity and a high avidity for IgG, in particular human IgG. By means of a high avidity this antibody can selectively ensure the recognition of human IgG in a complexed state by a multipoint binding.

One of the two receptors is bound according to the invention to a solid phase or is capable of binding to a solid phase and the other of the two receptors carries a signal-generating group or is capable of binding to a signal-generating group. In a preferred embodiment, the first receptor is bound to the solid phase or is capable of binding to the solid phase, and the second receptor carries the signal-generating group or is capable of binding to the signal-generating group. In another preferred embodiment the second receptor is bound to the solid phase or is capable of binding to the solid phase, and the first receptor carries the signal-generating group or is capable of binding to the signal-generating group.

All signal-generating groups familiar to a person skilled in the art can be used as a signal-generating group. A directly detectable group is preferably used, for example, a chemiluminescent, fluorescent or radioactive group or a metal sole, latex or gold particle. The signal-generating groups can be detected in a manner known to a person skilled in the art.

The first or second receptor capable of binding is preferably soluble and preferably carries a label which serves to bind the receptor. A partner of an X/anti-X binding system is preferred as the label, e.g., a partner of a combination selected from biotin/avidin, biotin/streptavidin, biotin/antibiotin, hapten/anti-hapten, Fc fragment of an antibody and antibody against this Fc fragment, an anti-antibody or carbohydrate and lectin. The other reaction partner of the binding system is bound to the carrier or to the signal-generating group. The partner of the binding system can be bound according to conventional methods known to a person skilled in the art. In this connection, a covalent as well as an adsorptive binding is suitable.

In a further embodiment the label is a signal-generating group as described herein. Preferably, a directly detectable group is used as a label. Methods for labelling the receptor are known in the art. The label is detected directly in a per se known manner by measuring the signal-generating group.

The label can also be detected in an indirect manner. In this case, a further binding partner which, in turn, is itself coupled to a signal-generating group, binds specifically to the receptor, to a label on the receptor, to the antigen and/or to a label on the antigen.

A most preferred embodiment of the method according to the invention is a method for the detection of antigen-specific antibodies of the immunoglobulin class G in a sample by means of an immunoassay in a one-step format comprising the steps:
  (a) contacting a sample which contains antibodies of the immunoglobulin class G which are specific for an antigen, with a first receptor which comprises an antigen in oligomeric or multimeric form and carries a signal-generating group, and with a second receptor which selectively binds antigen-bound, aggregated immunoglobulin G and carries a label, under conditions under which an immune complex consisting of antigen, immunoglobulins G specifically bound thereto and the second receptor is formed;
  (b) contacting the reaction mixture from (a) with a solid phase which contains an immobilized binding partner for the label of the second receptor under conditions under which the immune complex from (a) binds to the solid phase via the second receptor;
  (c) detecting the bound complex from (b) by means of the signal-generating group.

Another most preferred embodiment of the method according to the invention is a method for the detection of antigen-specific antibodies of the immunoglobulin class G in a sample by means of an immunoassay in a one-step format comprising the steps:
  (a) contacting a sample which contains antibodies of the immunoglobulin class G which are specific for an antigen, with a first receptor which comprises an antigen in oligomeric or multimeric form, wherein the first receptor carries a label, and with a second receptor which selectively binds antigen-bound, aggregated immunoglobulin G and carries a signal-generating group under conditions under which an immune complex consisting of antigen, immunoglobulins G specifically bound thereto and the second receptor is formed;
  (b) contacting the reaction mixture from (a) with a solid phase which contains an immobilized binding partner for the label of the first receptor under conditions under which the immune complex from (a) binds to the solid phase via the first receptor;
  (c) detecting the bound complex from (b) by means of the signal-generating group.

A further subject matter of the invention is a kit that is suitable for use in the method according to the invention described herein including the preferred embodiments.

A kit is preferred that comprises a first analyte-specific receptor and a second analyte-specific receptor wherein one of the two receptors is bound to a solid phase or is capable of binding to a solid phase and the other receptor carries a signal-generating group or is capable of binding to a signal-generating group, characterized in that the first analyte-specific receptor contains at least two binding sites for the analyte and the second analyte-specific receptor is capable of selectively binding to an arrangement of at least two analyte molecules, which are bound to the first receptor.

More preferred is a kit according to the invention wherein the first analyte-specific receptor and the second analyte-specific receptor are formulated for use in one reaction mixture.

A more strongly preferred embodiment concerns a kit in which the first receptor is bound to the solid phase or is capable of binding to the solid phase and the second receptor carries the signal-generating group or is capable of binding to the signal-generating group.

Another also more strongly preferred embodiment concerns a kit wherein the second receptor is bound to the solid phase or is capable of binding to the solid phase and the first receptor carries the signal-generating group or is capable of binding to the signal-generating group.

In a further preferred embodiment, the first receptor can also be provided in the kit according to the invention in the form of receptor precursors. The receptor precursors are described herein in connection with the method according to the invention. In particular, the kit can contain a bead as a receptor precursor and an additional receptor precursor, e.g., a peptide.

The kit according to the invention can also comprise a bead as a first receptor which comprises at least 10, at least 50 or at least 100 binding sites.

Another aspect according to the invention concerns the use of an analyte-specific receptor which contains at least two binding sites for the analyte in a method for determining an analyte in a sample. This method is preferably the method described herein, more preferably a diagnostic method described herein.

The invention is illustrated by the following examples. Each of the examples contains data according to the invention and comparative data that were obtained using methods of the prior art.

EXAMPLES

Example 1

Detection of Anti-Rubella-Specific Immunoglobulin G in Human Sera According to the Method and Comparison of the Sensitivity of the Method According to the Invention with an Immunoassay of the Prior Art in an Indirect Test Format with a Washing Step 1.1. METHOD ACCORDING TO THE INVENTION Anti-rubella IgG was detected immunologically in native sera using an automated ELECSYS® 2010 analyzer (Roche Diagnostics GmbH). Measurements were carried out using an antibody according to the invention as capture antibody. The biotin conjugate of this antibody was immobilized on the surface of streptavidin-coated magnetic beads and therefore binds anti-rubella IgG bound to a multimeric rubella-like particle (RLP) from a sample. The complex was detected by a ruthenylated monoclonal antibody which bound to the RLPs. The signal detection in the ELECSYS® 2010 analyzer was based on electrochemiluminescence.

The chromogenic ruthenium complex was bound to the solid phase in the presence of a specific immunoglobulin analyte and emitted light at 620 nm after excitation on a platinum electrode. The light signal is indicated in arbitrary units. The measurement was carried out using anti-rubella-IgG-positive samples from a panel with mixed titre and two seroconversion panels.

1.2 PRIOR ART

A two-step immunoassay (Cobas Core, Rubella IgG Recomb II) of the prior art was carried out for comparison.

Panels with Mixed Titre

| threshold | One-step immunoassay according to the invention coi < 1 neg coi ≥ 1 pos 3500 counts | | Two-step immunoassay <10 U/ml neg ≥10 IU/ml pos 10 IU/ml |
|---|---|---|---|
| sample | counts | COI | IU/ml |
| PTR 201-1 | 3867 | 1.1 | 20.8 |
| PTR 201-2 | 73943 | 21.1 | 144.8 |
| PTR 201-3 | 626833 | 179.1 | 134.8 |
| PTR 201-4 | 434690 | 124.2 | 300 |
| PTR 201-5 | 2268 | 0.65 | 0.4 |
| PTR 201-6 | 5371 | 1.53 | 19.6 |
| PTR 201-7 | 185186 | 52.9 | 15.4 |
| PTR 201-8 | 9367 | 2.68 | 26.4 |
| PTR 201-9 | 174982 | 50.0 | 129.1 |
| PTR 201-10 | 134451 | 38.4 | 84.5 |
| PTR 201-11 | 71459 | 20.4 | 56 |
| PTR 201-12 | 582819 | 166.5 | 300 |
| PTR 201-13 | 582257 | 166.4 | 109.1 |
| PTR 201-14 | 31982 | 9.1 | 22.2 |
| PTR 201-15 | 645934 | 184.6 | 300 |
| PTR 201-16 | 2250 | 0.64 | 1.2 |
| PTR 201-17 | 36001 | 10.3 | 64.9 |
| PTR 201-18 | 12711 | 3.6 | 16.5 |
| PTR 201-19 | 141224 | 40.3 | 12.1 |
| PTR 201-20 | 350990 | 100.3 | 155.3 |
| PTR 201-21 | 57148 | 16.3 | 91.1 |
| PTR 201-22 | 5030 | 1.4 | 28.7 |
| PTR 201-23 | 30672 | 8.8 | 66.6 |
| PTR 201-24 | 27950 | 8.0 | 8.3 |
| PTR 201-25 | 194719 | 55.6 | 142.5 |

Seroconversion Panels

| threshold | | One-step immunoassay according to the invention coi < 1 neg coi ≥ 1 pos 3500 counts | | Two-step immunoassay <10 U/ml neg ≥10 IU/ml pos 10 IU/ml |
|---|---|---|---|---|
| sample | day | counts | COI | IU/ml |
| RP 001-001 | 0 | 1767 | 0.50 | 0.8 |
| RP 001-002 | 2 | 1821 | 0.52 | 0.7 |
| RP 001-003 | 7 | 1833 | 0.52 | 0.4 |
| RP 001-004 | 9 | 1732 | 0.49 | 0.6 |
| RP 001-005 | 14 | 1880 | 0.47 | 0.5 |
| RP 001-006 | 17 | 2592 | 0.74 | 0.5 |
| RP 001-007 | 21 | 30305 | 8.66 | 3 |
| RP 001-008 | 24 | 76058 | 21.73 | 5.7 |
| RP 001-009 | 28 | 203264 | 58.08 | 13.8 |
| RP 001-010 | 31 | 293043 | 83.73 | 23.7 |
| RP 001-011 | 35 | 262759 | 75.07 | 23.8 |
| RP 001-012 | 38 | 194288 | 55.51 | 16.3 |
| RP 001-013 | 42 | 181673 | 51.91 | 16.3 |
| RP 001-014 | 45 | 160403 | 45.83 | 14.4 |
| RP 001-015 | 50 | 139584 | 39.88 | 18.1 |
| RP 011-001 | 0 | 1902 | 0.54 | 0 |
| RP 011-002 | 3 | 1766 | 0.50 | 0.2 |
| RP 011-003 | 9 | 1753 | 0.50 | 0 |

-continued

| | | One-step immunoassay according to the invention coi < 1 neg coi ≥ 1 pos 3500 counts | | Two-step immunoassay <10 U/ml neg ≥10 IU/ml pos 10 IU/ml |
|---|---|---|---|---|
| threshold | | | | |
| sample | day | counts | COI | IU/ml |
| RP 011-004 | 12 | 1720 | 0.49 | 0.1 |
| RP 011-005 | 18 | 3928 | 1.12 | 0.4 |
| RP 011-006 | 19 | 92242 | 26.35 | 7.7 |
| RP 011-007 | 24 | 366359 | 104.57 | 28.8 |
| RP 011-008 | 27 | 408392 | 116.88 | 37.4 |
| RP 011-009 | 31 | 405799 | 115.94 | 33.9 |
| RP 011-010 | 36 | 417007 | 119.14 | 39.1 |
| RP 011-011 | 39 | 414958 | 118.55 | 38 |
| RP 011-012 | 43 | 385813 | 110.23 | 44.4 |
| RP 011-013 | 46 | 398357 | 113.82 | 52.8 |

Positive titres in the seroconversion panels could be detected on the $21^{st}$ and $18^{th}$ day, respectively, in the one-step method and not until the $28^{th}$ and $24^{th}$ day, respectively, in the two-step method.

The immunoassay format according to the invention is more sensitive than the two-step immunoassay of the prior art because detection of a positive titre is possible at an earlier time.

Example 2

Comparison of the Performance of an Anti-Human IgG Antibody Receptor Having Properties According to the Invention (Low Affinity, Selective Binding of Aggregated Human IgG) with an Anti-Human IgG Antibody Receptor Having Properties of the Prior Art (High Affinity, Equally Strong Binding of Aggregated and Non-Aggregated IgG)

Master calibrators (MC), negative and positive sera were tested for anti-rubella IgG antibodies using the immunological method according to example 1.

| | Mab<h-IgG>IgM type low affinity coi < 1 neg coi ≥ 1 pos 6859 counts | | Mab<h-IgG-IgG type high affinity coi < 1 neg coi ≥ 1 pos 3521 counts | |
|---|---|---|---|---|
| Sample | Counts | COI | counts | COI |
| MC1 0 IU/ml | 2399 | 0.35 | 1483 | 0.42 |
| MC2 10 IU/ml | 6859 | 1.00 | 3521 | 1.00 |
| MC3 50 IU/ml | 35617 | 5.19 | 3385 | 0.96 |
| MC4 150 IU/ml | 170048 | 24.79 | 6027 | 1.71 |
| MC5 300 IU/ml | 334483 | 48.76 | 10946 | 3.11 |
| neg. 700-1899 | 2349 | 0.34 | 1269 | 0.36 |
| neg. 705-2814 | 2171 | 0.32 | 1308 | 0.37 |
| pos. 1810 | 287386 | 41.90 | 5291 | 1.50 |
| pos. 1851 | 55348 | 8.07 | 1666 | 0.47 |

In the present example, the susceptibility to interference of the test according to the invention by free IgG was examined. The result column on the left shows that free IgG which is always present in a human serum sample does not interfere with the test so that a high test sensitivity is achieved. The capture antibody which is directed against human, aggregated IgG and has a low affinity, does not bind free IgG or only to a negligible extent. Thus, only aggregated IgG is bound to the solid phase which can then, in turn, be detected as anti-rubella-specific IgG by means of binding to a multimeric/multivalent Rubella antigen ("Rubella-like particles") and detection by a ruthenylated anti-Rubella MAB.

In contrast, the results for a test procedure according to the prior art are shown in the right hand column in Example 2. In the prior art the capture antibody does not discriminate between aggregated and non-aggregated, i.e., free IgG. Hence, free as well as aggregated IgG is bound to the solid phase. In the subsequent binding of the Rubella antigen and the detection reaction, this evidently decreases the sensitivity of the test. The sample MC4 has a value of 24.79 for the test procedure according to the invention, whereas the same sample only reaches a value of 1.71 with the prior art method, i.e., only narrowly exceeds the cut-off index of 1.

The difference becomes very clear in the last two lines of the result table and, in particular, in the last line. The serum "pos. 1851" is clearly anti-rubella positive (value: 8.07) with the method of the invention, whereas the prior art method classifies the same sample as negative, i.e., falsely negative (value 0.47, i.e., under the cut-off index of 1).

The lack of sensitivity of the prior art method could thus have fatal consequences because positive samples are falsely detected as negative.

The results clearly show that the use of a receptor antibody according to the invention enables a more sensitive detection of anti-rubella antibodies compared with a receptor antibody of the prior art.

Example 3

Detection of Anti-Rubella IgG Antibodies in Human Serum Samples which Contain Rheumatoid Factor Commercial human serum samples (Bioclinical Partners) which contain rheumatoid factor were tested for anti-rubella IgG antibodies using the method according to the invention described in example 1.

A two-step immunoassay (Cobas Core, rubella IgG recomb II) of the prior art was carried out as a comparative experiment.

| | One-step immunoassay according to the invention coi < 1 neg coi ≥ 1 pos 3254 counts | | Two-step immunoassay <10 U/ml neg ≥10 IU/ml pos 10 IU/ml | Rheumatoid factor |
|---|---|---|---|---|
| threshold | | | | |
| sample | counts | COI | IU/ml | IU/ml |
| BCP 9808-114-04673 | 141077 | 43.35 | 103.76 | 24 |
| BCP 9808-114-04674 | 765 | 0.24 | 3.53 | 353 |
| BCP 9808-114-04675 | 173111 | 53.19 | 208.43 | 429 |
| BCP 9808-114-04676 | 167319 | 51.41 | 82.80 | 186 |
| BCP 9808-114-04677 | 153119 | 47.05 | 124.57 | 324 |
| BCP 9808-114-04678 | 82728 | 25.42 | 42.28 | 189 |
| BCP 9808-114-04679 | 164793 | 50.64 | >300 | 400 |
| BCP 9808-114-04680 | 171594 | 52.73 | 204.08 | 185 |
| BCP 9808-114-04681 | 5696 | 1.75 | 11.18 | 56 |
| BCP 9808-114-04682 | 64006 | 19.67 | 65.89 | 272 |
| BCP 9808-114-04683 | 167373 | 51.43 | 146.24 | 56 |
| BCP 9808-114-04684 | 138037 | 42.42 | 71.94 | 40 |
| BCP 9808-114-04685 | 166660 | 51.21 | 187.39 | 139 |
| BCP 9808-114-04686 | 79085 | 24.30 | 85.52 | 315 |

The results clearly show that the method according to the invention correctly classifies the samples despite the presence of rheumatoid factor.

What is claimed is:

1. A method for determining an analyte in a sample wherein the analyte is an antigen-specific antibody of the immunoglobulin class G (IgG), said method comprising the steps of:
 (a) contacting the sample with a first analyte-specific receptor, said receptor comprising an antigen comprising at least two epitopes for the analyte, and a second analyte-specific receptor, said receptor comprising an antibody having low affinity and high avidity for the analyte, such that binding of at least two of the analyte molecules to the first receptor forms an arrangement and selective binding of the second receptor to the arrangement forms an immune complex, wherein one of the two receptors is bound to a solid phase or is capable of binding to a solid phase and the other receptor carries a signal-generating group or is capable of binding to a signal-generating group, and
 (b) determining the presence or/and the amount of the analyte by detecting the signal-generating group on the solid phase while not detecting either free IgG that is non-specific for the antigen or free, uncomplexed Ig that is specific for the antigen,
  wherein the at least two analyte molecules bound to the first receptor are aggregated, and wherein steps (a) and (b) are carried out in one reaction mixture without a washing step.

2. The method according to claim 1 wherein the first receptor is bound to the solid phase or is capable of binding to the solid phase and the second receptor carries the signal-generating group or is capable of binding to the signal-generating group.

3. The method according to claim 1 wherein the second receptor is bound to the solid phase or is capable of binding to the solid phase and the first receptor carries the signal-generating group or is capable of binding to the signal-generating group.

4. The method according to claim 1 wherein the first receptor contains at least two different binding sites, at least two identical binding sites or a combination of different and identical binding sites for the analyte.

5. The method according to claim 1 wherein the first receptor is an oligomeric or a multimeric receptor.

6. The method according to claim 1 wherein the first receptor comprises a bead.

7. The method according to claim 1 wherein the first receptor is provided in the form of receptor precursors.

8. The method according to claim 7, wherein the receptor precursors are of such a nature that they can associate with one another or bind to one another during or before the contacting step in order to form the first receptor.

9. The method according to claim 1 wherein the second receptor is an antibody that binds to aggregated or oligomerized immunoglobulin.

10. The method according to claim 1 wherein the second receptor is an antibody with at least two paratopes.

11. The method according to claim 1 wherein the second receptor is an antibody of the immunoglobulin class M.

12. The method according to claim 1 wherein the second receptor is a monoclonal antibody.

* * * * *